US 8,465,721 B2

(12) United States Patent
Edwards et al.

(10) Patent No.: US 8,465,721 B2
(45) Date of Patent: Jun. 18, 2013

(54) BIOSYNTHESIS OF NANOPARTICLES

(75) Inventors: Chad D. Edwards, Carmel, IN (US); Daniel D. Lefebvre, Kingston (CA)

(73) Assignee: Queen's University at Kingston, Kingston, ON (CA)

( * ) Notice: Subject to any disclaimer, the term of this patent is extended or adjusted under 35 U.S.C. 154(b) by 0 days.

(21) Appl. No.: 13/310,335

(22) Filed: Dec. 2, 2011

(65) Prior Publication Data
US 2012/0164062 A1 Jun. 28, 2012

Related U.S. Application Data

(60) Provisional application No. 61/419,401, filed on Dec. 3, 2010.

(51) Int. Cl.
*C01B 17/00* (2006.01)
*C01B 19/04* (2006.01)
*C01G 9/08* (2006.01)
*C01G 11/02* (2006.01)
*C12P 3/00* (2006.01)

(52) U.S. Cl.
USPC ........ 423/509; 423/566.1; 435/168; 977/773; 977/774; 977/894

(58) Field of Classification Search
USPC ................. 423/509, 566.1; 435/168; 977/773, 977/774, 894
See application file for complete search history.

(56) References Cited

U.S. PATENT DOCUMENTS

| 2009/0246519 A1* | 10/2009 | Hanson | 428/364 |
| 2010/0055199 A1* | 3/2010 | Mansoori | 424/618 |
| 2011/0135932 A1* | 6/2011 | Mester et al. | 428/402 |
| 2012/0108425 A1* | 5/2012 | Gnanamangai et al. | 504/117 |

OTHER PUBLICATIONS

The English abstract of CN 102134579 a published on Jul. 27, 2011.*
Bao, H., et al., "Extracellular microbial synthesis of biocompatible CdTe quantum dots", Acta Biomaterialia 6, 3534-3541 (2010).
Bai, H.J., et al., "Biosynthesis of cadmium sulfide nanoparticles by photosynthetic bacteria *Rhodopseudomonas palustris*", Colloids and Surfaces B: Biointerfaces 70, 142-146 (2009).
Cui, R., et al., "Living Yeast Cells as a Controllable Biosynthesizer for Fluorescent Quantum Dots", Advanced Functional Materials 19, 2359-2364 (2009).
Lefebvre, D., et al., "Decontaminating heavy metals from water using photosynthetic microbes", in Emerging Environmental Technologies vol. II, 57-73 (2009).

(Continued)

*Primary Examiner* — Timothy Vanoy

(57) ABSTRACT

This invention provides a method of biosynthesizing nanoparticles and quantum dots. The method may comprise culturing photosynthetic cells and/or fungal cells of a multicellular fungus in a culture medium comprising one or more species of metal in ionic or non-ionic form; and one or more counter elements to the one or more species of metal, or one or more compound comprising one or more counter elements to the one or more species of metal; wherein the cells biosynthesize nanoparticles and quantum dots incorporating the metal. The invention also provides biosynthesized nanoparticles and quantum dots.

21 Claims, 8 Drawing Sheets

OTHER PUBLICATIONS

Kelly, D.J.A., et al., "Biotransformation of mercury in pH-stat cultures of eukaryotic freshwater algae", Archives of Microbiology 187, 45-53 (2007).

Kelly, D.J.A., et al., "The biotransformation of mercury in pH-stat cultures of microfungi", Canadian Journal of Botany 84, 254-260 (2006).

Gross, W., et al., "Ecophysiological studies on the red alga Galdieria sulphuraria isolated from southwest Iceland", Plant Biol. 1, 694-700 (1999).

Dameron, C.T., et al., "Biosynthesis of cadmium sulphide quantum semiconductor crystallites", Nature 338, 596-597 (1989).

Rippka, R., et al., "A cyanobacterium which lacks thylakoids", Archives of Microbiology 100, 419-436 (1974).

Siegel, L.M., "A direct microdetermination for sulfide", Anal. Biochem. 11, 126-132 (1965).

Sueoka, N., "Mitotic replication of deoxyribonucleic acid in *Chlamydomonas reinhardi*", PNAS 46, 83-91 (1960).

Allen, M.B., "Studies with Cyanidium caldarium, an anomalously pigmented chlorophyte", Archiv. für Mikrobiologie 32, 270-277 (1959).

* cited by examiner

BIOSYNTHESIS OF NANOPARTICLES

RELATED APPLICATION

This application claims the benefit of the filing date of U.S. Provisional Patent Application No. 61/419,401, filed on 3 Dec. 2010, the contents of which are incorporated herein by reference in their entirety.

FIELD

This invention relates to biological synthesis of nanoparticles. In particular, the invention relates to biological synthesis of quantum dots.

BACKGROUND

A quantum dot (QD) is a nanocrystal or nanoparticle that ranges from 1-50 nanometers (approximately 5-250 atoms) in diameter or longest dimension. Quantum dots are composed of semiconductor material, however their small size results in characteristics that differ significantly from other semiconductor material. For example, the quantum containment effect of QDs produces emission and absorption spectra that vary with their composition, shape, and geometry. The quantum containment effect also produces discrete electron energy levels with transitions between states similar to atoms. As a result, quantum dots have unique and desirable behaviours that permit new technological and scientific applications. For example, the size of a quantum dot has a large impact on the energy bands of the dot, such that smaller quantum dots have higher band gaps and as a result produce higher energy light emissions during photoluminescence. Quantum dots are useful in optical, chemical, electronic, and photoelectrochemical applications, such as in solar cells, light emitting diodes (LEDs), and flat panel displays, and are of considerable value in the growing field of nanotechnology.

However, QDs are difficult and expensive to synthesize, particularly at an industrial scale. Known methods are either laboratory scale, suitable for obtaining small quantities of QDs (e.g., for research purposes), and/or they are expensive.

For example, QDs may be synthesized by using lateral patterns in remotely doped quantum wells or semiconductor heterostructures, thereby forming them from 2-dimensional electron or hole gases. These are essentially only of experimental interest with applications involving electrical currents.

In another process, spontaneous nucleation of self-assembled QDs occurs under specific conditions in both metallorganic vapour phase and molecular beam epitaxy. Islands of material thus formed become covered to make QDs. This method of manufacturing is expensive and is mainly of interest for quantum cryptography and quantum computation.

Viral assembly of QDs has been reported. Biocomposite structures were made using M13 bacteriophage viruses because such genetically engineered viruses can associate with semiconductor surfaces. Viruses can take the form of liquid crystals that are susceptible to change through their own concentrations in and the ionic strength of their solvent as well as applied magnetic fields. Therefore the association properties of viruses with other materials can be exploited through their liquid crystals to form inorganic nanocrystals such as QDs. This process is suitable for only very limited scale production.

In another example, electrochemical assembly of nanostructures such as QDs in a highly ordered fashion may occur spontaneously through ionic reactions at metal-electrolyte interfaces. These well ordered nanostructures can then be placed on a substrate from the metal surface. This process is used primarily as a way to study effects of the arrangement of the nanostructures.

In another example, high temperature dual injection is used to produce small quantities of QDs. This process is not practical for large scale production.

Larger quantities of QDs are produced in a highly scalable manner involving seed templates that are molecular clusters. Chemical precursors are converted into nanoparticles on these seed templates or points of nucleation which are stable. This method does not need the high temperature of the previously described dual injection system. However, the cost of this process is substantial. Another method of QD synthesis uses simultaneous increasing of the precursor concentration, but it requires further development.

What is needed is a more efficient and economical process for synthesizing quantum dots and nanoparticles.

SUMMARY

Described herein is a method of biosynthesizing a nanoparticle in a medium comprising: (i) at least one member selected from the group consisting of cells, extracellular molecules, protein, denatured protein, carbohydrate, and cellular debris; (ii) one or more elements selected from, but not restricted to, Periodic Table groups 15 and 16, or one or more compounds comprising one or more elements selected from, but not restricted to, Periodic Table groups 15 and 16; and (iii) one or more metal in ionic or non-ionic form selected from, but not restricted to, Periodic Table groups 11, 12, 13, and 14; wherein nanoparticles incorporating the metal are synthesized. The cells may be photosynthetic cells, non-photosynthetic cells, or a combination thereof. The photosynthetic cells may be selected from cyanobacteria, algae, and plant cells, and combinations thereof. The non-photosynthetic cells may be selected from bacteria and fungi cells, and combinations thereof. The protein may be an enzyme. The protein may be derived from, e.g., secreted, from a cell. The denatured protein may be derived from, e.g., secreted, from a cell. The carbohydrate may be derived from, e.g., secreted, from a cell.

Also described herein is a method of biosynthesizing a nanoparticle; comprising: growing and/or maintaining (i.e., culturing) photosynthetic cells and/or fungal cells of a multicellular fungus in a culture medium comprising: (i) one or more elements selected from, but not restricted to, Periodic Table groups 15 and 16, or one or more compounds comprising one or more elements selected from, but not restricted to, Periodic Table groups 15 and 16, and (ii) one or more metal in ionic or non-ionic form selected from, but not restricted to, Periodic Table groups 11, 12, 13, and 14; wherein the cells biosynthesize nanoparticles incorporating the metal.

In some embodiments the one or more element is/are selected from sulfur, selenium, tellurium, arsenic, antimony, and bismuth, and the one or more metal is/are selected from copper, zinc, cadmium, indium, gallium, silver, gold, germanium, and lead.

The concentration of the one or more elements may be elevated relative to a concentration in a standard culture medium. For example, the concentration of one or more of sulfur, selenium, tellurium, arsenic, antimony, and bismuth may be 2× to 100× times or more the concentration of one or more of sulfur, selenium, tellurium, arsenic, antimony, and bismuth in the standard culture medium.

The method may comprise growing and/or maintaining the photosynthetic cells under conditions that allow the cells to perform photosynthesis. The method may comprise growing and/or maintaining the photosynthetic cells under conditions that do not allow the cells to perform photosynthesis.

The nanoparticle may be a quantum dot.

In some embodiments the metal ions may be derived from one or more of copper, zinc, cadmium, indium, and gallium.

The photosynthetic and/or non-photosynthetic cells may be prokaryotic cells and/or eukaryotic cells.

The method may further comprise isolating or recovering nanoparticles from the cells. Isolating and/or recovering nanoparticles from the cells may comprise: acidifying the culture medium to induce cellular flocculation; and centrifuging the obtained cellular flocculent to concentrate the nanoparticles.

The method may further comprise manipulating one or more variables during the biosynthesis, wherein the variables are selected from: concentration of the one or more metals; ratio of two or more metals; concentration the one or more elements; duration of exposure of the cells to the one or more metals; pH, temperature and/or pressure of the bioreactor; one or more constituents of the culture medium; oxic or anoxic conditions including any variation between these conditions; and light intensity, including substantially no light (i.e., darkness); wherein manipulation of the one more variables determines a characteristic of the nanoparticle. The characteristic may be size, shape, or composition of the nanoparticle.

Also described herein is a method of biosynthesizing a layered nanoparticle; comprising: (a) growing and/or maintaining photosynthetic and/or non-photosynthetic cells and/or fungal cells of a multicellular fungus in a culture medium comprising: (i) one or more elements selected from, but not restricted to, Periodic Table groups 15 and 16, or one or more compounds comprising one or more elements selected from, but not restricted to, Periodic Table groups 15 and 16; and (ii) one or more species of metal in ionic or non-ionic form; (b) subsequently growing and/or maintaining the cells in a culture medium comprising: (iii) one or more elements selected from, but not restricted to, Periodic Table groups 15 and 16, or one or more compounds comprising one or more elements selected from, but not restricted to, Periodic Table groups 15 and 16; and (iv) one or more species of metal in ionic or non-ionic form, wherein at least one species of metal is different from that used in (ii); wherein the cells biosynthesize nanoparticles incorporating the metal of (ii) in a first layer and the metal of (iv) in a second layer. In some embodiments the element may be one or more of sulfur, selenium, and tellurium, or one or more compound comprising one or more of sulfur, selenium, and tellurium. The metal may be selected from, but not restricted to, Periodic Table groups 11, 12, 13, and 14. In some embodiments the metal is selected from copper, zinc, cadmium, indium, and gallium.

The method may further comprise repeating step (b) a selected number of times with different metals so as to biosynthesize a nanoparticle with a selected number of layers, each layer comprising a selected one or more species of metal. The nanoparticle may be a quantum dot.

Also provided herein is a nanoparticle produced as described herein. The nanoparticle may comprise at least one metal selected from, but not restricted to, Periodic Table groups 11, 12, 13, and 14. In some embodiments the metal is selected from copper, zinc, cadmium, indium, and gallium.

Also provided herein is a quantum dot produced as described herein. The quantum dot may comprise at least one metal selected from, but not restricted to, Periodic Table groups 11, 12, 13, and 14. In some embodiments the metal is selected from copper, zinc, cadmium, indium, and gallium.

BRIEF DESCRIPTION OF THE DRAWINGS

For a better understanding of the invention, and to show more clearly how it may be carried into effect, embodiments will be described, by way of example, with reference to the drawings, wherein.

DETAILED DESCRIPTION OF EMBODIMENTS

Figure 1:
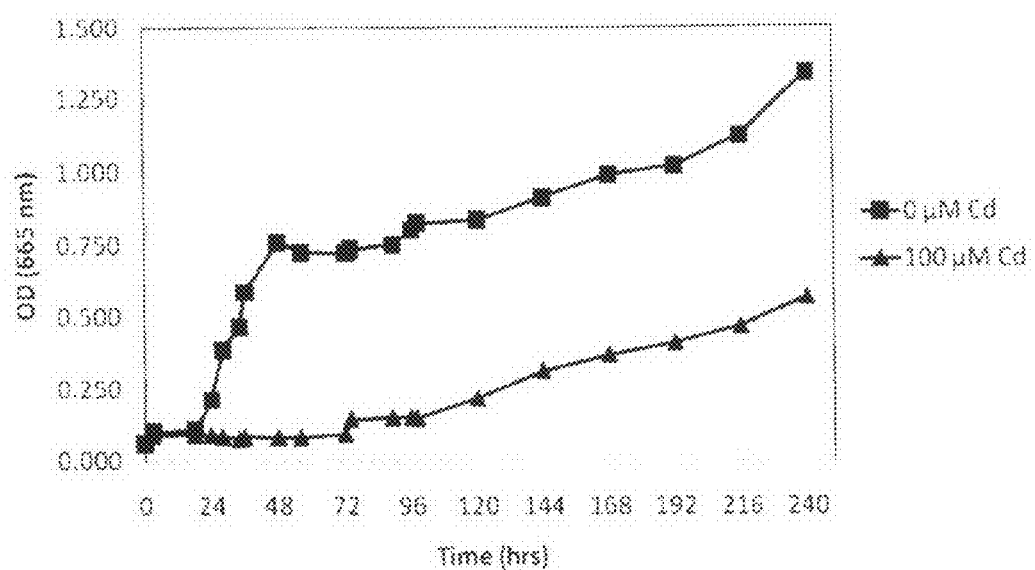
FIG. 1 is a plot showing growth curves of the green alga *Chlamydomonas reinhardtii* in response to the presence of cadmium as Cd(II) in the growth medium.

Previously-known techniques for physical and chemical manufacturing of nanoparticles and quantum dots are generally inefficient and expensive. For example, using previous methods it may cost several thousand dollars to make one gram of nanoparticles of small and consistent enough size to be of use. Further, previous methods generally are not environmentally-friendly.

Described herein are methods for biosynthesizing nanoparticles and quantum dots that overcome the drawbacks of previous methods. Compared to previously-known methods, the methods described herein are simple and inexpensive, and capable of producing large quantities of nanoparticles and QDs within a short time. Furthermore, the biosynthetic methods described herein are substantially environmentally-friendly. Quantum dots produced as described herein may be useful in a variety of applications, including, but not limited to, lasers, light-emitting diodes, optoelectronics, solar cells, display technologies, and in vitro bioimaging.

As used herein, the term "nanoparticle" is considered to be equivalent to the term "nanocrystal", and refers to a particle having a dimension between 1 and 100 nanometers in at least one dimension. A nanoparticle may or may not exhibit one or more size-related properties that differ significantly from those observed in larger particles or bulk materials.

As used herein, the term "quantum dot" refers to a nanoparticle having a dimension between 1 and 50 nanometers in at least one dimension, wherein the quantum dot comprises a fluorescent semiconductor material in which electron propagation is confined in three dimensions.

As described herein, biosynthesis of nanoparticles and QDs may be carried out by photosynthetic cells or fungi cells, or combinations thereof The photosynthetic cells may be prokaryotic or eukaryotic. The prokaryotic photosynthetic cells may include photosynthetic bacteria such as, but not limited to, cyanobacteria. The eukaryotic photosynthetic cells may be unicellular organisms or cells of multicellular organisms, including, but not limited to, algae, lichens, liverworts, mosses, and vascular plants. Biosynthesis of nanoparticles including QDs as described herein may be carried out by photosynthetic cells living and/or growing under conditions where the cells can carry out photosynthesis. Alternatively, biosynthesis of nanoparticles including QDs as described herein may be carried out by photosynthetic cells or other cells of photosynthetic organisms living and/or growing under conditions where the cells cannot or do not carry out photosynthesis. Such latter conditions may include, for example, the cells living and/or growing in low-light or darkness, and/or in low carbon dioxide such that photosynthesis is not possible. Further, biosynthesis of nanoparticles including QDs as described herein may be carried out by non-photosynthetic cells such as fungi.

Production of QDs by cells as described herein may be easily confirmed by optical detection (e.g., by detecting fluorescence). For example, detection may be carried out using a confocal microscope fitted with fluorescence detection equipment or a fluorometer. In embodiments described herein, a confocal microscope with appropriate spatial resolution allows detection of fluorescence of quantum dots. For example, a confocal microscope with a resolution of about 10 nm wavelength and a fluorometer with a spatial resolution of 4 nm or less wavelengths allows sampling of more than one quantum dot at a time. This may produce a smooth spectrum indicating the presence of quantum dots enriched for a particular size, or spectra having a broader nature and more than one maximum due to the presence of multiple sizes of QDs and/or irregularities in geometries of the QDs.

Prokaryotic heterotrophic bacteria have been shown to make gold, silver, and iron nanoparticles. However, biosynthesis of quantum dots using such organisms has not been demonstrated. Yeast, on the other hand, can produce CdS quantum dots and PbS nanocrystals. However, biosynthesis of quantum dots and nanoparticles using photosynthetic organisms and non-photosynthetic organisms such as multicellular fungi, as described herein, is hitherto unknown.

In some applications it may be desirable to connect quantum dots, either to each other directly, or to a matrix or substrate, or in a combination of such connections. The methods described herein provide for connections between QDs that involve organic compounds of various lengths. Such connections may impart different selected electrical and optical activities to interconnected QD structures. For example, the types of connections may control interactions between QDs. Synthesis of such connected QD structures is difficult and expensive using previously-known techniques. However, biosynthesis of QDs as described herein may provide a solution to the manufacture of large quantities of QDs, as well as provide an organic framework or substrate by which they are interconnected.

The methods described herein provide for biosynthesis of nanoparticles and quantum dots using photosynthetic cells such as bacteria, cyanobacteria, algal, and plant cells, and non-photosynthetic cells such as fungi. In various embodiments the synthesis may or may not be carried out in a cellular matrix. As noted above, biosynthesis of QDs embedded in a cellular matrix allows for control of connections between QDs.

The inventors have found that the diverse taxonomic groups of photosynthetic cells, such as algae and cyanobacteria cells, are capable of bio-transforming Hg(II), Cd(II), Zn(II) and Cu(II). For example, solutions may be detoxified with these organisms by precipitating the metals as HgS, CdS, ZnS, and CuS crystallites. Therefore, these four heavy metals, Hg, Cd, Zn, and Cu, share the same detoxification pathway, in which the metal ion is combined with a sulfur counterion. Results suggest that other metals, including those of Periodic Table groups 11, 12, 13, and 14, such as, for example, Ga and In, and indeed all metal ions share the same detoxification pathway. For example, Ga is not considered to be toxic and Ga containing QDs are promising for applications such as electronics as a result of their unique properties. Embodiments described herein are thus applicable to all metals.

In addition to sulfur (S), selenium (Se) and tellurium (Te), and combinations thereof, may also be used, among others, including elements selected from, but not restricted to, Periodic Table groups 15 and 16, as the counterion for the metal. For example, Se is metabolized in algae and plants in a manner similar to S; i.e., selenate is taken up and reduced like sulfate. These elements may be provided as reduced forms, for example, sulfate, selenate, and tellerate, or in any compound that provides S, Se, and Te to the cells and which can be used by the cells. For example, compounds comprising elements selected from, but not restricted to, Periodic Table groups 15 and 16 may be used.

As noted above, biosynthesis of nanoparticles and quantum dots may be carried out with cells of multicellular fungi. For example, studies with the multicellular fungi *Hymenoscyphus ericae, Neocosmospora vasinfecta*, and *Verticillium terrestre* indicated that these species are able to convert Hg(II) into HgS in a similar manner to that of algae. These results suggest that multicellular fungi cells are also able to biotransform other metal ions into sulfides. Thus, methods for biosynthetisis of nanoparticles and quantum dots as described herein include use of multicellular fungi.

Diatoms accumulate silica ($SiO_2$) as a structural element in their cell walls. This ability of diatoms to create silicaceous cell walls will provide a support matrix for QDs. This will also enable the simultaneous production of mesoporous silica and semiconductor quantum dots that can be combined biologically for applications in two distinct classes of nanostructured materials for optoelectronics and other applications. For example, studies with the diatom *Navicula pellicosa* indicated that this species is able to convert Hg(II) into HgS in a similar manner to that of other algae, suggesting that these cells are also able to biotransform other metal ions into sulfides. Thus, methods for biosynthesis of nanoparticles and quantum dots as described herein include use of diatoms.

In accordance with methods described herein, algae and cyanobacteria cells were subjected to relatively high exposure levels of Cd(II), Zn(II) and Cu(II) at up to 100 μM, at a density of 0.77 g wet weight cells/L. Cells were capable of biotansforming this concentration of metals into sulfides and surviving the treatments. For example, FIG. 1 shows growth curves of the green alga *Chlamydomonas reinhardtii* in response to the presence of cadmium as Cd(II) in the growth medium. The ability of this species to recover from metal treatments is explained by the production of CdS, shown in FIG. 2, which precipitates the metal and effectively detoxifies it.

Figure 2:
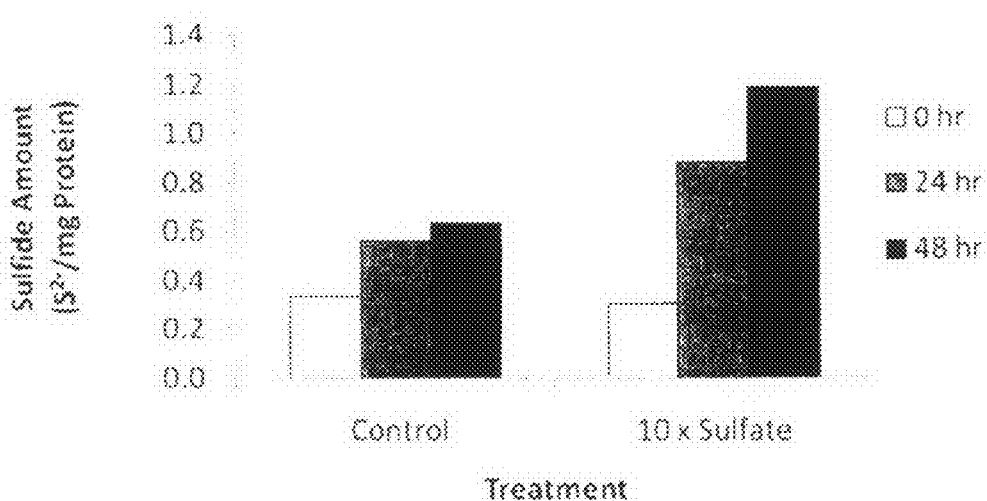
FIG. 2 is a plot showing production of CdS by *Chlamydomonas reinhardtii*.
Figure 3:
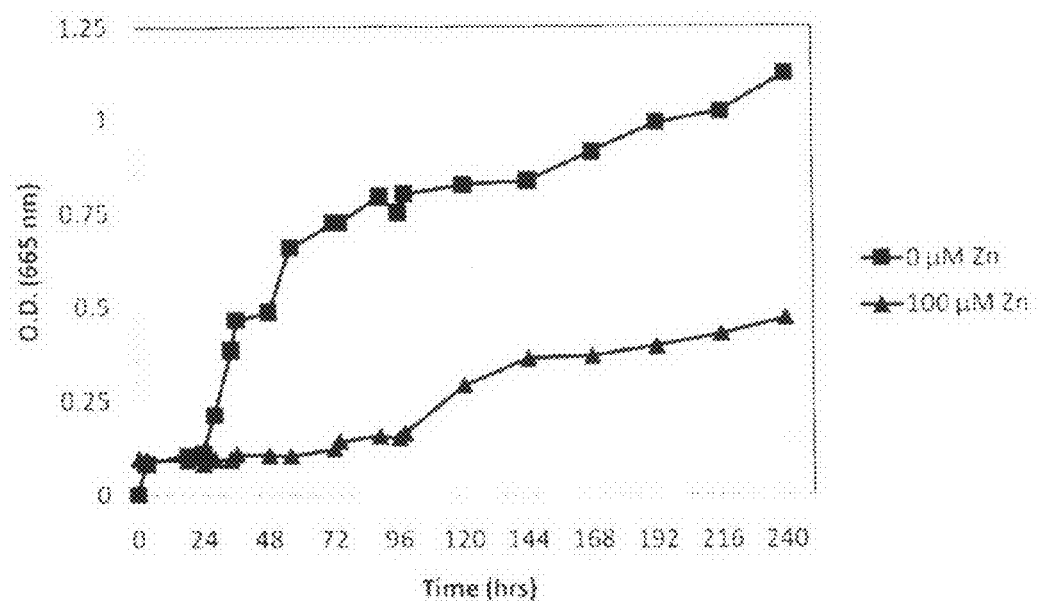
FIG. 3 is a plot showing growth curves of *Chlamydomonas reinhardtii* in response to the presence of cadmium as Zn(II) in the growth medium.
Figure 4:
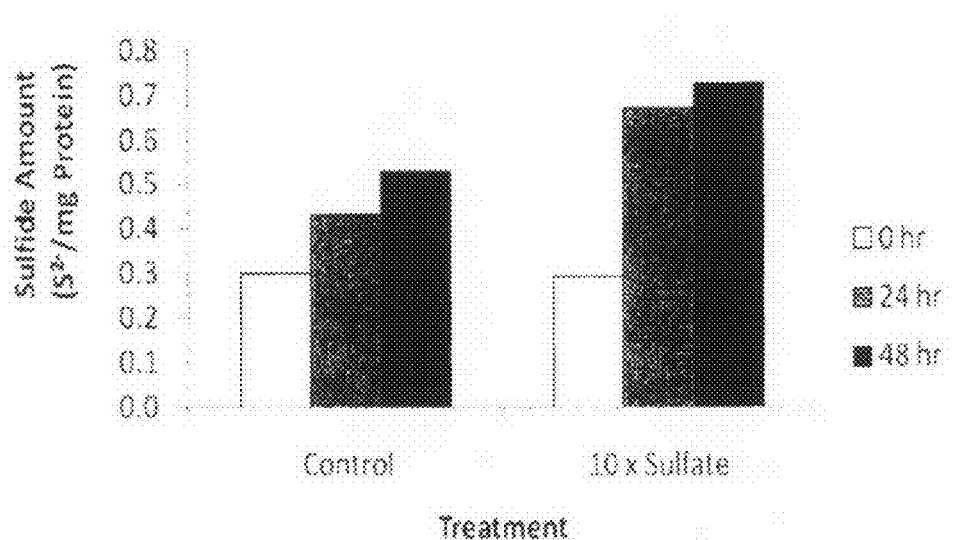
FIG. 4 is a plot showing production of ZnS by *Chlamydomonas reinhardtii*.

In accordance with methods described herein, cells may be grown in medium with a standard amount of S, Se, and/or Te as well as other counterion elements. "Standard amount" refers to the amount of the counterions such as but not limited to S, Se, and/or Te present in a growth medium not necessarily intended for biosynthesis of nanoparticles. However, supplementation of the culture with excess counterions such as S, Se, and/or Te permits the cells to biotransform larger quantities of metal ions resulting in an additional production of metal precipitate, including nanoparticles and/or quantum dots. For example, as shown in FIG. 2, excess sulfate ($SO_4^{2-}$) may be added to a standard sulphur-containing growth medium to increase production of CdS. For example, in the case of S, excess sulfate may be added so as to increase the concentration by 2×, 5×, 10×, 20×, 50×, 100×, or more than the concentration of sulfate in a standard growth medium. The same response with elevated sulfate is obtained for other metals ions, such as, for example, Zn(II) (see FIGS. 3 and 4). The sulfur or other counterion (i.e., Se, Te) may of course be added in any form or compound that may be used by the cells, sulfate being but one example for sulfur.

Cells may be grown in bioreactors at densities of over fifty times the above amount which, in turn, are able to cope with metal ion concentrations of over 5 mM. The exposure may be increased by one or two orders of magnitude by, for example, (1) supplementing with counterion-containing compounds such as sulfate (see FIGS. 2 and 4), and (2) giving the cells acute exposures to metal ion concentrations that would eventually kill the cells. The latter is acceptable because the cells have to be sacrificed anyway in order to collect and concentrate the QDs.

Using methods as described herein, yields of nanoparticles and quantum dots may be substantial. For example, in the green algae *Chlamydomonas reinhardtii*, yields of sulfides such as CdS and ZnS after 48 h cell exposure to Cd(II) and Zn(II), respectively, may be as high as 10 g per Kg dry weight of cells. However, some of the yield may not be in the form of QDs. Similar yields have been obtained in the cyanobacterium *Synecchococcus leopoliensis*, and the red algae *Cyanidioschyzon merolae*.

Figure 5:
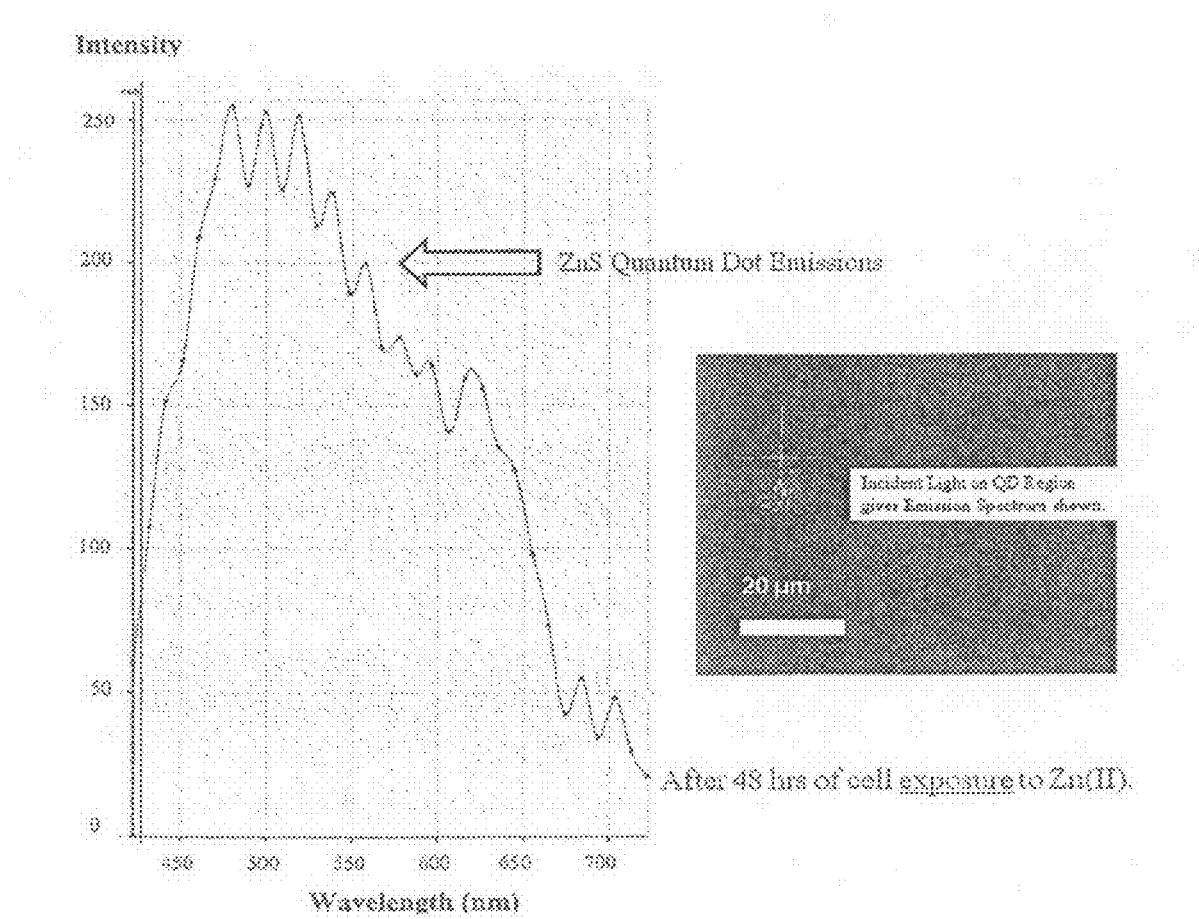
FIG. 5 is a plot showing emission spectrum of ZnS in *Chlamydomonas reinhardtii* exposed to an excitation wavelength of 405 nm, indicating quantum dot synthesis during cellular exposure to Zn(II).
Figure 9:
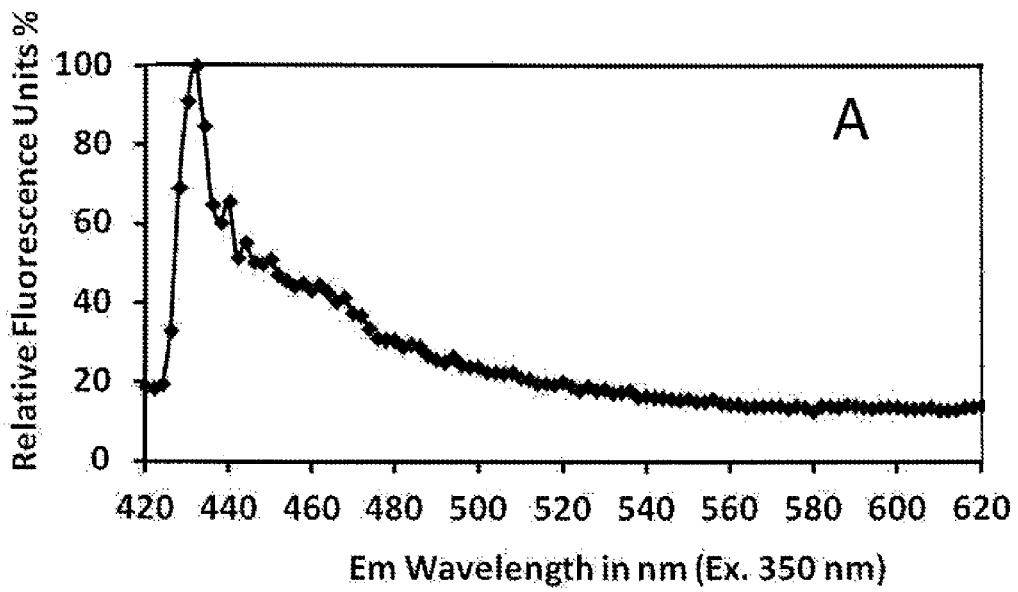
FIGS. 9A-C are plots showing fluorescence spectra of *Synechococcus leopoliensis* after (A) 48 hours, (B) 120 hours, and (C) 192 hours incubation with 5 mM sodium selenite and 1 mM zinc chloride, using an excitation wavelength of 350 nm.
Figure 9:
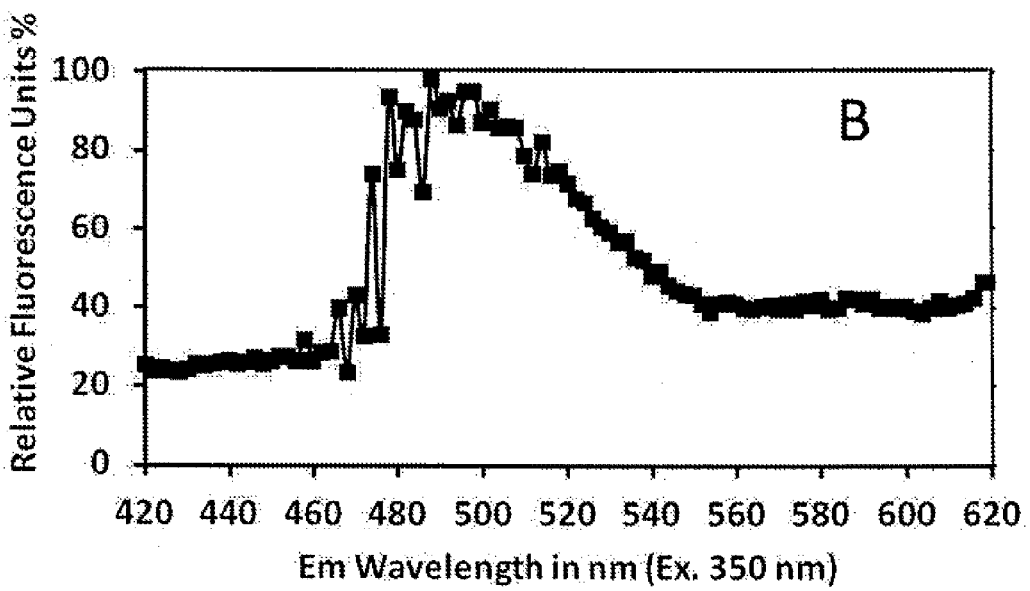
Figure 9:
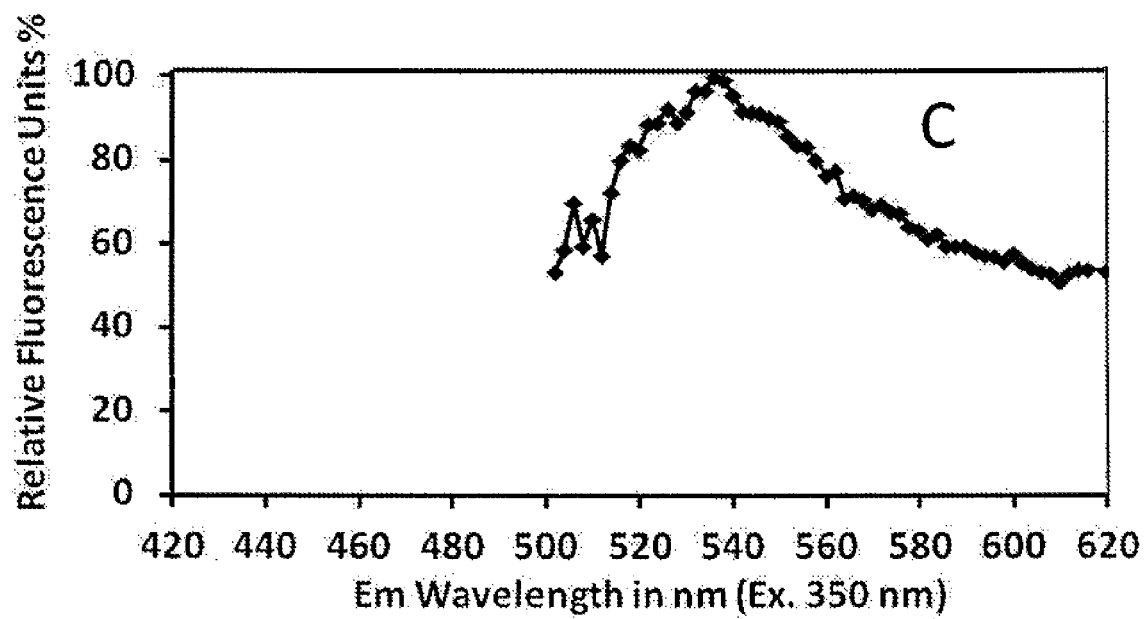

Quantum dots may be detected in metal-treated cells by exposure to excitation light at UV or visible wavelengths. For example, UV or a wavelength of about 405 nm causes the QDs to produce light emissions in the appropriate (i.e., visible) range. For example, FIG. 5 shows a plot of ZnS QD detection by emission wavelength in *Chlamydomonas reinhardtii* exposed to an excitation wavelength of 405 nm. The emission spectra may be measured at point sources within the cells, and the spatial resolution of the optical detection (e.g., confocal microscope) may be such that the scale of the fluorescing material is on the order of 50 to 100 nm. An excitation wavelength of 405 nm is suitable for photoluminesence of ZnS and CdS nanoparticles, however a lower (i.e., shorter) wavelength (higher energy) source such as in the UV range may also be used, so as to stimulate emissions from a wider range of quantum dot sizes. For example, FIGS. 9A-C show emission spectra of ZnSe QD produced by *Synecchococcus leopoliensis* upon excitation with 350 nm UV.

If the photosynthetic cells normally emit light at a wavelength close to the QD light emission spectrum, it may be difficult to detect the quantum dots. This can occur in algae and cyanobacteria that possess compounds such as nicotinamide adenine dinucleotide phosphate (NADPH) and phenylpropanoids (e.g., hydroxycinnamic acids) that emit similar wavelengths as quantum dots when, excited with UV light. Such cells also have pigments such as chlorophylls and carotenoids that absorb the fluorescent light produced by quantum dots. Therefore, it may be necessary to remove the pigments so that light emitted by the QDs can be detected. The pigments may be removed using one or more organic solvent extractions and/or by destroying interfering molecules. For example, acetone may be added to the cells in medium. This may be extracted with an equal volume of hexane and the solvents containing the pigments removed. This may be repeated and then the extracted cells dried under vacuum. The dried samples may then be taken up in water to measure their QD fluorescence spectra.

Various processes may be used to recover and/or isolate quantum dots from cells. For example, the induction of cellular floc through acidification of the cell culture media provides a rapid and efficient means of concentrating cellular metal sulfides in floating cellular debris. This procedure may repeated two or more times. Using this process substantially all (e.g., >98%) of the metals may be concentrated into floating skimmable material, and >99.6% may be concentrated with further centrifugation. This efficient removal process concentrates QDs while at the same time removes them from metal ions and other ions in the culture. Further steps may include subjecting the quantum dots to an acid wash, and removal of residual cellular debris (e.g., by heating or burning).

Other processes to recover and/or isolate quantum dots from cells may include 1) digestion of cellular constituents such as cell walls, 2) heat treatments of the cells, 3) acid treatment of the cells, and 4) ultrafine filtering. For example, cells from which pigments have been removed can be disrupted through homogenization and/or sonication, and then filtered such that the quantum dots pass through filters of 100-500 nm pore size, thereby separating the quantum dots from cellular debris.

Figure 6:
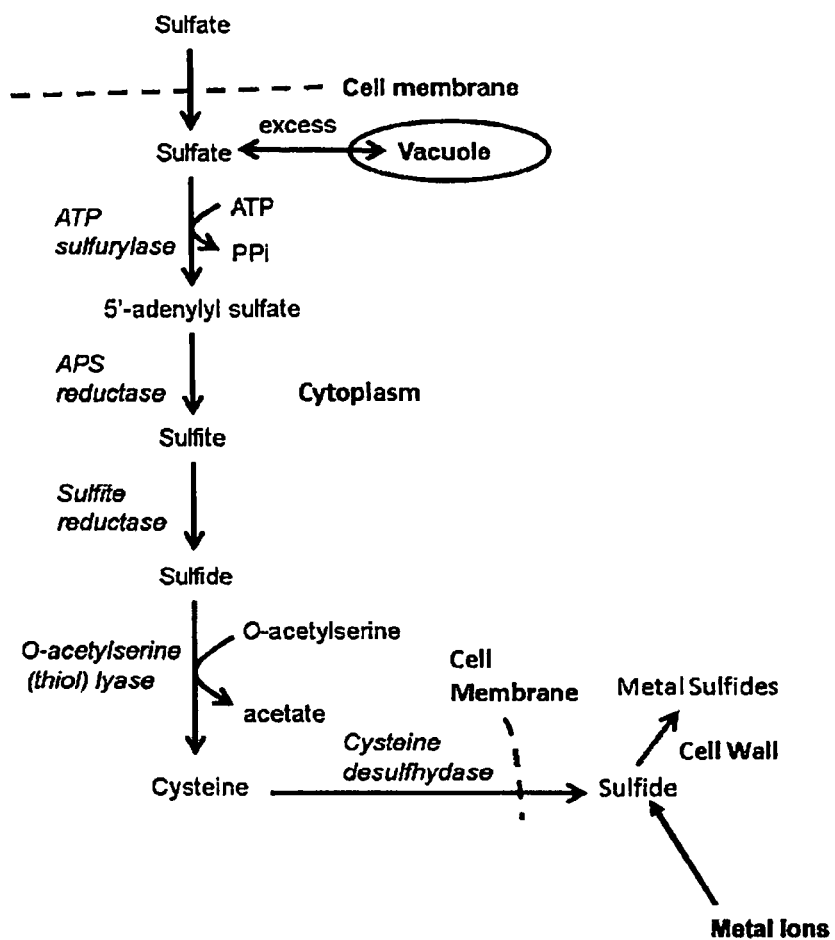
FIG. 6 is a flow chart showing the biochemical synthetic pathway for sulfides in algae and cyanobacteria (adapted from Lefebvre et al., 2009).

Such exemplary processes described above for isolating QDs from cell cultures indicate that QDs are associated with cellular constituents. It is likely that the sulfide that binds to metal ions at least in part comes into contact with metal ions at the cell membrane-cell wall interface, where applied metal ions would first encounter sulfide produced by the cells. The biochemical synthetic pathway for sulfides is shown in FIG. 6 (adapted from Lefebvre et al., 2009). Since cyanobacterial, algal, and plant cell walls variously include polysaccharides and peptidoglycans (polymers of sugars and amino acids), among others, these provide a variety of cellular matrices in which QDs could be embedded to provide the appropriate connections between QDs. Also, since diatoms have silicaceous cell walls, they provide a cellular matrix in which QDs could be embedded to provide the appropriate connections between QDs.

Biosynthesis of uniform sizes of QDs and selected sizes or ranges of sizes of QDs may be carried out by manipulating one or more variables in the biosynthesis. For example, one or more of the following may be manipulated:

addition of one or more materials (e.g., a chelating such as EDTA) or application of one or more variables to slow down, speed up, or stop the reaction;

concentration of one or more metals;

ratio of two or more metals;

concentration of the counterion(s) for the one or more metals, at or before metal addition;

duration of exposure of the cells to the one or more metals;

temperature and/or pressure of the bioreactor;

oxygen and/or carbon dioxide availability to the cells, pH of the medium constituents of the medium; and light intensity, including substantially complete darkness.

For example, increasing the duration of incubation of *Synecchococcus leopoliensis in* 5 mM sodium selenite and 1 mM zinc chloride increases the size of ZnSe quantum dots produced, with diameters averaging less than 2 nm at 48 hours, and about 3 nm after 192 hours, as indicated by the shift in emission peak wavelength with increasing incubation (see FIGS. 9A-C). Further, the type of cells used may be selected to produce QDs of a desired size or range of sizes. For example, larger cells are expected to make larger quantum dots than smaller cells. Thus, for example, algal species such as *Chlamydomonas rheinhardtii* and *Cyanidioschyzon merolae*, being larger than the cyanobacterium *Synecchococcus leopoliensis*, may produce larger quantum dots. In addition, manipulation of any of the above variables may also be done to optimize production efficiency.

Further, nanoparticles and quantum dots comprising a combination of materials in a selected arrangement may be prepared by carrying out biosynthesis in stages, wherein each stage may include use of different materials. For example, a quantum dot comprising layers of different metals or different combinations of metals may be prepared by carrying out successive biosynthetic stages, wherein each stage uses a different metal or combination of metals. Quantum dots comprising homogeneous mixtures of two or more metals may be prepared by combining the metals during biosynthesis. The metals and combinations thereof may be used with various anion substrates or combinations of one or more such substrates.

Thus, the methods described herein are suitable for simultaneous synthesis of mixed metal quantum dots. The simultaneous production of QDs from different metals in a single system is desirable where, for example, multiple emission wavelengths are sought, or when capturing the energy of photons with different energy levels is required. Biosynthesis of QDs using a combination of cell types, e.g., two or more of cyanobacteria, algae, and plant cells, as described herein is amenable to mixed metal synthesis processes through parallel and/or sequential exposure to selected metal substrates.

Biosynthetic methods described herein may be scaled-up for mass QD production. For example, a kilogram wet weight of algal or cyanobacterial cells can produce up to 1.0 g of metal sulfide. For the green algae *Chlamydomonas rheinhardtii* at a cellular density of 0.1 $O.D._{665}$, 1300 L of culture would be required. However, the inventors have grown these cells at up to 50 times this density which equates to a bioreactor volume of only 26 L. Such bioreactor size is not difficult to implement in virtually any setting. Because photosynthetic and fungal cells such as, but not limited to, those exemplified herein, have high tolerances to the metal ions, which is believed to arise from their elevated rates of metal biotransformation and their amenability to easy culture, they are suitable for use in photobioreactor-based and dark bioreactor-based QD production.

Embodiments of the invention are further described by way of the following non-limiting examples.

Example 1

Methods according to one embodiment, applied to three species of photosynthetic organisms, are described below.

1.1 Culture Sources and Growth Conditions

The eukaryotic alga *Chlamydomonas reinhardtii* (UTEX 90) was obtained from the Culture Collection of Algae, University of Texas at Austin. Cultures were grown in high salt medium (HSM) (Sueoka, 1960) composed of 9.35 mM $NH_4Cl$, 8.27 mM $K_2HPO_4$, 5.44 mM $KH_2PO_4$, 0.09 mM $CaCl_2$, 0.081 mM $MgSO_4.7H_2O$, 3 µM $H_3BO_3$, 2.1 µM $MnCl_2.4H_2O$, 1 µM $Na_2EDTA.2H_2O$, 0.6 µM $FeCl_3.6H_2O$, 0.03 µM $NaMoO_4.2H_2O$, 0.025 µM $ZnCl_2$, 0.01 µM $CoCl_2.6H_2O$, 0.07 nM $CuCl_2.2H_2O$ in double deionized water.

*Synechococcus leopoliensis* (UTEX 2434), a cyanobacteria species, was obtained from the Culture Collection of Algae, University of Texas at Austin. Cells were grown in medium using 50× Cyanobacteria BG-11 Freshwater Solution (Sigma Aldrich, catalogue #C3061) (Rippka et al., 1974) that was diluted to 1× in double deionized water to final concentrations of: 17.65 mM $NaNO_3$, 0.3 mM $MgSO_4.7H_2O$, 0.24 mM $CaCl_2.2H_2O$, 0.18 mM $K_2HPO_4$, 46.0 µM $H_3BO_3$, 31 µM citric acid, 21 µM ferric ammonium citrate, 9.1 µM $MnCl_2.4H_2O$, 2.8 µM $MnNa_2EDTA$, 1.7 µM $NaMoO_4.2H_2O$, 0.77 µM $ZnSO_4.7H_2O$, 0.32 µM $CuSO_4.5H_2O$, 0.17 µM $Co(NO_3)_2.6H_2O$.

The red algae *Cyanidioschyzon merolae* 10D was acquired from the Microbial Culture Collection of the National Institute for Environmental Studies (Tsukuba, Japan). *C. merolae* cultures were plated and grown in a *Cyanidium* medium (Allen, 1959) composed of 9.85 mM $(NH_4)_2SO_4$, 2.06 mM $K_2HPO_4$, 1.01 mM $MgSO_4.7H_2O$, 0.67 mM $CaCl_2$, 13 µM $Na_2EDTA$, 3.0 µM $H_3BO_3$, 2.2 µM $FeCl_3.6H_2O$, 1.2 µM $MnCl_2.4H_2O$, $CuSO_4.5H_2O$, 0.22 µM $ZnSO4.7H_2O$, 0.12 µM $Na_2MoO_4$ and 0.05 µM $CoCl_2.6H_2O$ in double deionized water. The medium was adjusted to pH 3.5 with HCl.

All chemicals were obtained from Sigma-Aldrich (Oakville, Canada) or Fisher Scientific (Ottawa, Canada).

Figure 7:
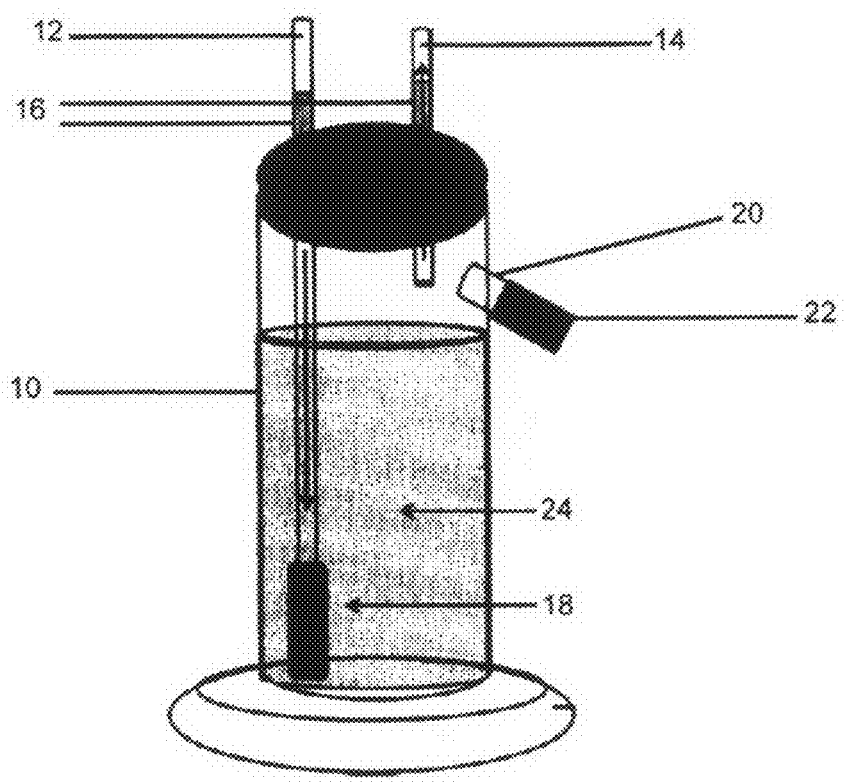
FIG. 7 is a schematic diagram of a bioreactor according to an embodiment described herein.

*S. leopoliensis*, and *C. reinhardtii* were grown in 1.5 L pyrex glass bioreactors (FIG. 7) under fluorescent lighting of 150 µEinsteins/m²/s at 27° C. for 18 hour photoperiods. As shown in FIG. 7, the bioreactor 10 had air inlet tube 12 and an air outlet tube 14, although aerating the cell culture is optional. Each tube was fitted with a sterile filter 16. The air inlet tube 12 extended toward the bottom of the bioreactor 10, and was fitted with an air stone 18. The reactor had a spout 20 with removable cap 22. Cells were kept suspended in 1 L culture 24 by aerating at a 1 L per min flow rate. *C. merolae* was grown similarly except that the temperature was maintained at 45° C. (Gross et al., 1999).

For all three species, supplemental sulfate was added to create a ten times increase in the level of sulfur from the original media. $K_2SO_4$ stock solution was 277.5 mM.

1.2 Supplemental Treatment

The treatment groups were as follows:

(i) Control: The cultures were grown in unmodified algal growth media.

(ii) 10× sulfate: Cultures were supplemented with $K_2SO_4$ to yield a ten times increase in the amount of sulfur at the time of metal exposure.

All treatments were performed in 100 mL of media in glass cell culture jars with translucent magenta caps. Illumination was 300 µEinsteins/m²/s with 120 rpm rotary shaking. Temperatures were 27° C. for *S. leopoliensis* and *C. reinhardtii* and 45° C. for *C. merolae*. All cultures started at a cell density of $O.D._{665}$=0.1.

1.3 Heavy Metal Treatment

The cells were exposed to divalent metal ions added to the media as $CdCl_2$ or $ZnCl_2$. Stocks containing 5 g/L were stored at 4° C. until used.

1.4 Metal Toxicity

Cell cultures were grown in bioreactors for 240 h with or without supplementation with 10× sulfate, beginning at a cell density of $O.D._{665}$=0.1 to a late log phase of growth ($O.D._{665}$≈1.0). Aliquots from the cultures were diluted in fresh media back to an optical density of 0.1 under sterile conditions with their respective media. One hundred mL cell cultures from each of the three groups were transferred into 150 mL glass cell culture jars, to which either Cd(II) or Zn(II) was added from metal chloride stock solutions. These culture jars were then vigorously stirred using an orbital shaker (VWR) at 120 rpm for 1 min under constant light, before 200 µL aliquots from each jar were distributed into the wells of sterile 96 well spectrophotometer plates (Costar 9017). The 96 well plates were incubated at 300 µEinsteins/m$^2$/s with a photo period of 18 h. The temperatures were as described for the bioreactors. Cultures were continuously shaken on an orbital shaker (VWR) at 120 rpm. Cellular growth was measured three times daily for 10 days using a Spectra Max Plus Spectrophotometer (Molecular Devices, Sunnyvale, Calif.).

1.5 Metal Sulfide Analysis

Acid labile sulfide analysis followed the protocol developed by Siegel, (1965) with several minor modifications. One hundred µL samples described above were used for the determination of sulfide content. These were transferred into 1.5 mL microcentrifuge tubes. To this was added 100 µL 0.02M N,N-dimethyl-p-phenylenediamine sulfate in 7.2 N HCl and 0.1 mL of 0.3 M FeCl$_3$ in 1.2 N HCl. Parafilm™ was used to seal the microcentrifuge cap, followed by an incubation of 20 min at room temperature, in the dark. Any precipitate that formed was removed by centrifugation at 10,000×g at room temperature for 10 minutes. Two hundred microliters of the remaining supernatant was then transferred into the wells of a 96 well plate and optical density was measured at 670 nm. Total sulfide concentration was determined by comparison with a Na$_2$S standard curve.

1.6 Microscopy and Quantum Dot Visualization

Live cells were placed in cell media on glass microscope slides with cover slips and viewed with a Carl Zeiss LSM 710 NLO Laser Scanning Confocal/Multiphoton Microscope. In both Cd(II)- and Zn(II)-treated cells, quantum dots were visualized when they were exposed to an excitation wavelength of 405 nm that caused light emissions in the appropriate range. Emission spectra and digital photographs were obtained.

Example 2

The methods described in Example 1, or variations thereof, may be applied to diatoms. For example *Navicula pelliculosa* (available from Ward's Natural Science, Rochester, N.Y.; Cat. #86 W 1210) may be grown in a general algal medium (AM) amended for diatoms by adding 50 mM Na$_2$SiO$_3$.9H$_2$O.

The general algal medium was composed of 3 mM NaNO$_3$, 0.15 mM MgSO$_4$.7H$_2$O, 0.12 mM CaCl$_2$, 0.12 mM K$_2$HPO$_4$, 95 µM Na$_2$CO$_3$, 46 µM Na$_2$EDTA, 42 µM FeSO$_4$.7H$_2$O, 2 µM H$_3$BO$_3$, 0.4 µM MnSO$_4$.4H$_2$O, 0.04 µM ZnSO$_4$.7H$_2$O, 0.04 µM AlK(SO$_4$)$_2$.12H$_2$O, 0.04 µM KBr, 0.04 µM Ni(NH$_4$)$_2$(SO$_4$)$_2$.6H$_2$O, 0.02 µM CuSO$_4$.5H$_2$O, 0.02 µM Co(NO$_3$)$_2$.6H$_2$O, 0.02 µM KI, 0.02 µM Cd(NO$_3$)$_2$.4H$_2$O, 0.005 µM VSO$_4$.2H$_2$O, 0.004 µM Na$_2$WO$_4$.2H$_2$O, 0.004 µM Cr(NO$_3$)$_2$.7H$_2$O, and 0.003 µM (NH$_4$)$_6$Mo$_7$O$_{24}$.4H$_2$O (Kelly et al., 2007). Growth was similar to other algae at pH 6.5.

Example 3

The methods described in Example 1, or variations thereof, may be applied to cells of multicellular fungi.

Isolates

*Hymenoscyphus ericae* (ATCC 32985) and *Neocosmospora vasinfecta* (ATCC 11686) were maintained on 2% malt extract agar (MEA; Difco, VWR Canlab, Mississauga, ON). *Verticillium terrestre* was isolated from sediments of the St. Mary's River (Sault Ste. Marie, Canada) collected downstream from local steel and pulp and paper factories. A 50-mL core sediment sample was homogenized in 250 mL sterile 1.5% agar in a sterile Vertis blender and diluted serially from 1/100 to 1/10,000. Aliquots of 0.5 mL of each dilution were plated onto the surface of a defined medium (DM) containing 20 g agar, 15 g dextrose, 4 g KNO$_3$, 1 g MgSO$_4$.H$_{22}$PO$_4$, 0.1 g CaCl$_2$, and 0.1 g NaCl, per L H$_2$0, and trace elements.

Growth of Fungi for Biotransformation Experiments

Fungi were grown in DM lacking agar and maintained in shaking cultures at 25° C. and pH 6.5. All experiments employed the pH-stat culturing technique described by Kelly and colleagues (2007), but without the provision of a light source. The growth of liquid cultures was monitored spectrophotometrically at O.D.$_{660}$ and application of Hg(II) as HgCl$_2$ was conducted at a standard O.D.$_{660}$ of 0.30 (Kelly et al., 2006).

Example 4

This example relates to the production of zinc selenide (ZnSe) quantum dots by the cyanobacterium *Synechococcus leopoliensis*. Cells were grown either 1) normally or 2) by starving cells for sulfur prior to exposure to selenite so that the cells would be forced to incorporate selenium into molecules that should lead to ZnSe quantum dot formation. This was then followed by exposure of either 1) selenite followed by zinc exposure or 2) simultaneous exposure of selenite and zinc. Results indicated that normally growing cells exposed simultaneously to selenite and zinc produced quantum dots at a high rate.

Cells were extracted with organic solvents to remove cellular pigments. An equal volume of acetone was added to the cells in medium. This was then extracted with an equal volume of hexane and the solvents containing the pigments were removed. This was repeated before the extracted cells were dried under vacuum. The dried samples were then taken up in water to measure their fluorescence spectra.

Figure 8:
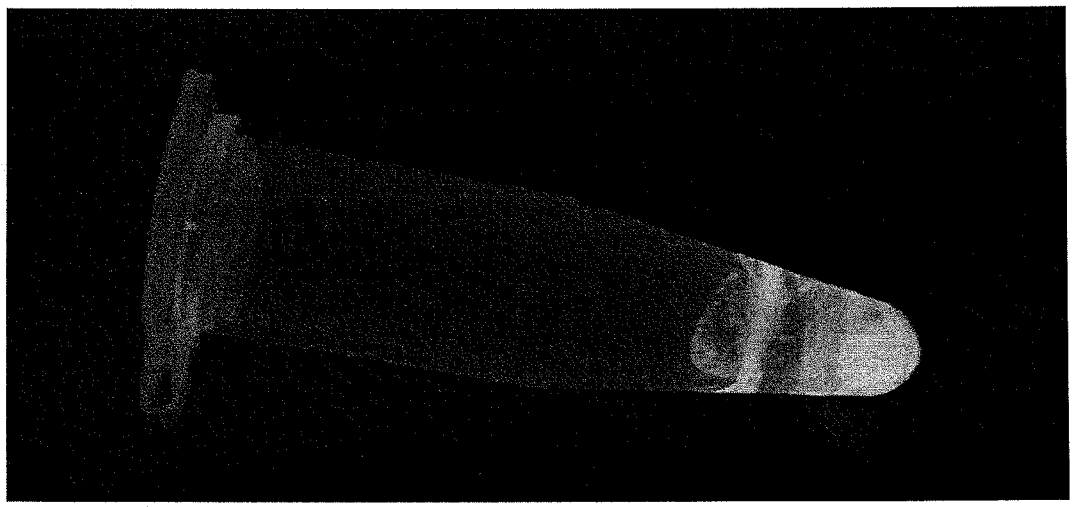
FIG. 8 is a photograph showing UV excited fluorescence of *Synechococcus leopoliensis* after being incubated simultaneously with 5 mM sodium selenite and 1 mM zinc chloride for 120 hours, using an excitation wavelength of 312 nm.

Results are shown in FIG. 8, which is a fluorescence image produced by an excitation wavelength of 312 nm of *Synechococcus leopoliensis* after 120 hours simultaneous incubation with 5 mM sodium selenite and 1 mM zinc chloride. Blue-green fluorescence indicating ZnSe quantum dots of average diameter of 2-3 nm was detected using UV incident wavelength of 312 nm prior to taking the photograph.

A time course of the fluorescence spectra of the *S. leopoliensis* cells upon excitation with 350 nm UV incident wavelength is plotted in FIGS. 9A, B, and C, after incubation for 48, 120, and 192 hours (respectively) with 5 mM sodium selenite and 1 mM zinc chloride. This result indicates that the peak emission ($\lambda_{max}$) shifted towards the red end of the spectrum with time as the quantum dots grew, possibly by the Ostwald ripening process. After 48 hours the quantum dots are small, e.g., less than 2 nm in diameter. After 120 hours the emission is in the blue-green range, indicating an average diameter approaching 3 nm in size.

EQUIVALENTS

Those of ordinary skill in the art will recognize, or be able to ascertain through routine experimentation, equivalents to the embodiments described herein. Such equivalents are within the scope of the invention and are covered by the appended claims.

REFERENCES

Allen, M. B. (1959) Studies with *Cyanidium caldarium*, an anomalously pigmented chlorophyte. *Arch. Microbiol.* 32:270-277.

Gross, W., & Oesterhelt, C. (1999) Ecophysiological studies on red alga *Galdieria sulphuraria* isolated from soutwest iceland. *Plant Biol.,* 1:694-700.

Kelly, D. J. A., Budd, K., & Lefebvre, D. D. (2006) The biotransformation of mercury in pH-stat cultures of microfungi. Canadian Journal of Botany 84: 254-260.

Kelly, D. J. A., Budd, K., & Lefebvre, D. D. (2007) Biotransformation of mercury in pH-stat cultures of eukaryotic freshwater algae, Archives of Microbiology 187: 45-53.

Lefebvre, D., & Edwards, C. (2009) Decontaminating heavy metals using photosynthetic microbes. in Emerging Environmental Technologies, Vol. II, Vishal Shah, Ed. Springer: 57.

Rippka, R., Waterbury, J., & Cohen-Bazire, G. (1974) A cyanobacterium which lacks thylakoids. *Arch. Microbiol.,* 100:419-436.

Siegel, L. M. (1965) A direct microdetermination of sulfide. *Anal. Biochem.* 11:126-132.

Sueoka, N. (1960) Mitotic replication of deoxyribonucleic acid in *Chlamydomonas reinhardii. PNAS,* 46:83-91.

The invention claimed is:

1. A method of biosynthesizing a nanoparticle; comprising:
    culturing photosynthetic cells under conditions that cause the cells to perform photosynthesis in a culture medium comprising:
    (i) one or more elements of Periodic Table groups 15 and 16, or one or more compounds comprising one or more elements of Periodic Table groups 15 and 16; and
    (ii) one or more species of metal in ionic or non-ionic form; wherein the cells biosynthesize nanoparticles incorporating the metal.

2. The method of claim 1, wherein a concentration of the one or more elements of Periodic Table groups 15 and 16, or the one or more compounds comprising one or more elements of Periodic Table groups 15 and 16, is elevated relative to a concentration in a standard culture medium.

3. The method of claim 2, wherein the concentration is 2× to 100× times, or greater than 100×, the concentration in the standard culture medium.

4. The method of claim 1, wherein the conditions that cause the cells to perform photosynthesis include culture medium substantially without a carbon or energy source.

5. The method of claim 1, further comprising recovering nanoparticles from the cells.

6. The method of claim 5, wherein recovering nanoparticles from the photosynthetic cells comprises:
    acidifying the culture medium to induce cellular flocculation; and
    centrifuging the obtained cellular flocculent to concentrate the nanoparticles.

7. The method of claim 1, wherein the nanoparticles include quantum dots.

8. The method of claim 1, wherein the metal ions are derived from one or more elements of Periodic Table groups 11 to 14.

9. The method of claim 1, wherein the photosynthetic cells are prokaryotic cells.

10. The method of claim 1, wherein the photosynthetic cells are eukaryotic cells.

11. The method of claim 1, wherein the photosynthetic cells are a combination of prokaryotic cells and eukaryotic cells.

12. The method of claim 1, comprising manipulating one or more variables during the biosynthesis, wherein the variables are selected from:
    concentration of one or more metals;
    ratio of two or more metals;
    concentration of the one or more elements of Periodic Table groups 15 and 16, or the one or more compounds comprising one or more elements of Periodic Table groups 15 and 16;
    duration of exposure of the cells to the one or more metals;
    oxygen and/or carbon dioxide availability to the cells;
    pH of the medium;
    temperature and/or pressure of the bioreactor;
    one or more constituents of the culture medium; and
    light intensity;
    wherein manipulation of one more variables determines a characteristic of the nanoparticle.

13. The method of claim 12, wherein the characteristic is size of the nanoparticle.

14. The method of claim 13, wherein the nanoparticle is a quantum dot.

15. A method of biosynthesizing a layered nanoparticle; comprising:
    (a) culturing photosynthetic cells under conditions that cause the cells to perform photosynthesis in a culture medium comprising:
    (i) one or more elements of Periodic Table groups 15 and 16, or one or more compounds comprising one or more elements of Periodic Table groups 15 and 16; and
    (ii) one or more species of metal in ionic or non-ionic form;
    (b) subsequently culturing the cells under conditions that cause the cells to perform photosynthesis in a culture medium comprising:
    (iii) one or more elements of Periodic Table groups 15 and 16, or one or more compounds comprising one or more elements of Periodic Table groups 15 and 16; and
    (iv) one or more species of metal in ionic or non-ionic form, wherein at least one species of metal is different from that used in (ii);
    wherein the cells biosynthesize nanoparticles incorporating the metal of (ii) in a first layer and the metal of (iv) in a second layer.

16. The method of claim 15, further comprising repeating step (b) a selected number of times with different metal so as to biosynthesize a nanoparticle with a selected number of layers, each layer comprising a selected one or more species of metal.

17. The method of claim 15, wherein the nanoparticle is a quantum dot.

18. A nanoparticle produced according to the method of claim 1.

19. The nanoparticle of claim 18, wherein the nanoparticle comprises at least one metal selected from copper, zinc, cadmium, indium, and gallium.

20. A quantum dot produced according to the method of claim 1.

21. The quantum dot of claim 20, wherein the quantum dot comprises at least one metal selected from copper, zinc, cadmium, indium, and gallium.

* * * * *